(12) United States Patent
Clement et al.

(10) Patent No.: US 8,308,775 B2
(45) Date of Patent: Nov. 13, 2012

(54) METHOD FOR ROTATING A VERTEBRA OR VERTEBRAE

(75) Inventors: Jean-Luc Clement, La Colle sur Loup (FR); Vincent Fiere, Collonge Au Mont d'Or (FR)

(73) Assignee: Medicrea International, Neyron (FR)

( * ) Notice: Subject to any disclaimer, the term of this patent is extended or adjusted under 35 U.S.C. 154(b) by 261 days.

(21) Appl. No.: 12/578,071

(22) Filed: Oct. 13, 2009

(65) Prior Publication Data

US 2010/0094350 A1 Apr. 15, 2010

Related U.S. Application Data

(60) Provisional application No. 61/105,334, filed on Oct. 14, 2008.

(51) Int. Cl.
*A61B 17/88* (2006.01)
(52) U.S. Cl. .................................. 606/279; 606/278
(58) Field of Classification Search .................. 600/246, 600/250–260, 264–266, 270, 272, 274, 277–279; 606/246–279
See application file for complete search history.

(56) References Cited

U.S. PATENT DOCUMENTS

| | | | | |
|---|---|---|---|---|
| 5,312,404 A * | 5/1994 | Asher et al. | ...... | 606/264 |
| 5,735,852 A * | 4/1998 | Amrein et al. | ...... | 606/278 |
| 5,879,351 A * | 3/1999 | Viart | ...... | 606/264 |
| 6,050,997 A * | 4/2000 | Mullane | ...... | 606/250 |
| 6,248,107 B1 * | 6/2001 | Foley et al. | ...... | 606/264 |
| 6,267,765 B1 | 7/2001 | Taylor et al. | | |
| 2003/0028191 A1* | 2/2003 | Shluzas | ...... | 606/61 |
| 2003/0176862 A1* | 9/2003 | Taylor et al. | ...... | 606/61 |
| 2004/0092930 A1* | 5/2004 | Petit et al. | ...... | 606/61 |
| 2005/0010215 A1* | 1/2005 | Delecrin et al. | ...... | 606/61 |
| 2005/0070901 A1* | 3/2005 | David | ...... | 606/61 |
| 2005/0096654 A1* | 5/2005 | Lin | ...... | 606/61 |
| 2006/0149234 A1* | 7/2006 | de Coninck | ...... | 606/61 |
| 2006/0167455 A1 | 7/2006 | Clement et al. | | |
| 2006/0200132 A1* | 9/2006 | Chao et al. | ...... | 606/61 |
| 2007/0173817 A1* | 7/2007 | Sournac et al. | ...... | 606/61 |
| 2008/0195150 A1* | 8/2008 | Bishop | ...... | 606/246 |
| 2009/0012565 A1* | 1/2009 | Sachs et al. | ...... | 606/246 |

* cited by examiner

*Primary Examiner* — Alvin Stewart
*Assistant Examiner* — Atiya Mahmud
(74) *Attorney, Agent, or Firm* — Young & Thompson

(57) ABSTRACT

A method for rotating a vertebra or vertebrae in a spine that is curved using a vertebral osteosynthesis device that includes polyaxial screws, linking rods, clamping parts, tightening nuts, and set screws. The method includes the steps of: implanting two series of the screws, clamping parts, and linking rods; completely tightening the tightening nuts of a first series of screws on the convex side of the spine curvature; completely tightening the set screws of a second series of screws on the concave side of the spine curvature; tightening the tightening nuts of the second series; and tightening the set screws of the first series.

4 Claims, 6 Drawing Sheets

METHOD FOR ROTATING A VERTEBRA OR VERTEBRAE

This application claims priority from U.S. Provisional Application 61/105,334 filed Oct. 14, 2008, which is incorporated by reference.

BACKGROUND OF THE INVENTION

It is known to correct deformations of the spine, such as scoliosis or kyphosis, in the frontal plane and/or the sagittal plane. Generally, a correction in a transverse plane (i.e., a plane perpendicular to the axis of the spine) is not carried out, although such a correction may also be desirable.

When a correction in the transverse plane is required, it is known to use a vertebrae adjusting device to exert a torque on the vertebrae and to maintain the vertebrae in the corrected position until the vertebrae are fixed with vertebral fixing equipment including anchoring screws and linking rods. However, this technique has the disadvantage of exerting great transverse stress on screws attached to the vertebrae, inducing a risk of weakening of the anchoring of these screws in the vertebrae, or even ruptures of the vertebrae. Moreover, the surgeon has difficulty precisely evaluating the amount of stress applied.

SUMMARY OF THE INVENTION

An object of the invention is to provide a novel method of rotating one or more vertebra without inducing a risk of weakening of the anchoring of the screws fixed to the vertebrae or of rupture of the vertebrae.

A further object of the invention is to provide a novel method that does not include additional leverage instruments connected to the vertebrae.

A yet further object of the invention is to provide a novel method of rotating one or more vertebra in a progressive and controlled way.

A still further object of the invention is provide a novel method for rotating a vertebra or vertebrae in a spine that is curved using a vertebral osteosynthesis device that includes polyaxial screws, linking rods, clamping parts, tightening nuts, and set screws, where the method includes implanting two series of the screws, clamping parts, and linking rods; tightening the tightening nuts of a first series of screws on the convex side of the spine curvature; tightening the set screws of a second series of screws on the concave side of the spine curvature; tightening the tightening nuts of the second series; and tightening the set screws of the first series.

These and other objects and advantages of the invention will be apparent to those of skill in the art of the present invention after consideration of the following drawings and description of preferred embodiments.

DESCRIPTION OF PREFERRED EMBODIMENTS

Figure 4:
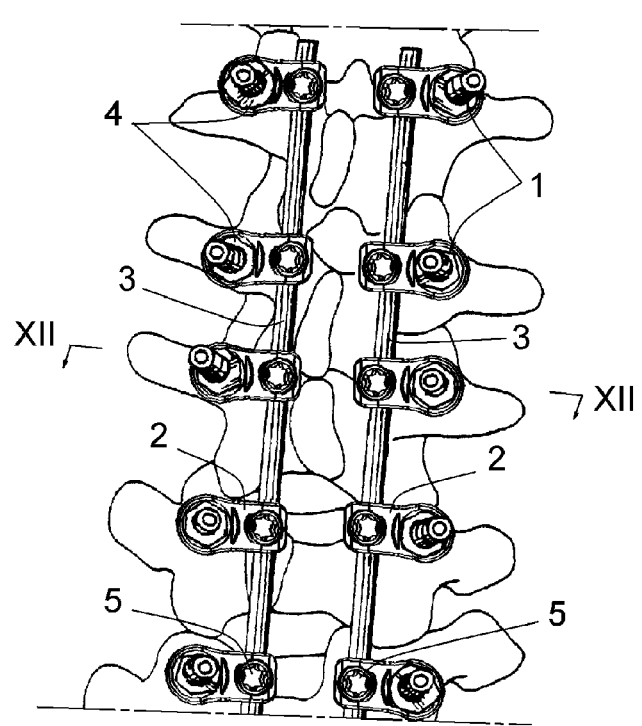
FIG. 4 is a posterior view of this part of spine after implantation of the vertebrae adjusting device.

FIG. 4 shows a device usable in the method of the present invention to rotate a vertebra or vertebrae, the device including polyaxial screws 1, clamping parts 2, linking rods 3, tightening nuts 4, and set screws 5.

In some embodiments, the polyaxial screws 1, linking rods 3 and tightening nuts 4 may be as described in U.S. Pat. No. 6,267,765, the contents of which are incorporated herein by reference. As disclosed in this document and as shown on FIG. 5, each of the polyaxial screws 1 has an anchoring distal part intended to be anchored to a pedicle of a vertebrae 100 and a bearing portion 12 articulated with respect to the anchoring distal part. The anchoring distal part has a threaded portion 11 on a proximal part.

Figure 1:
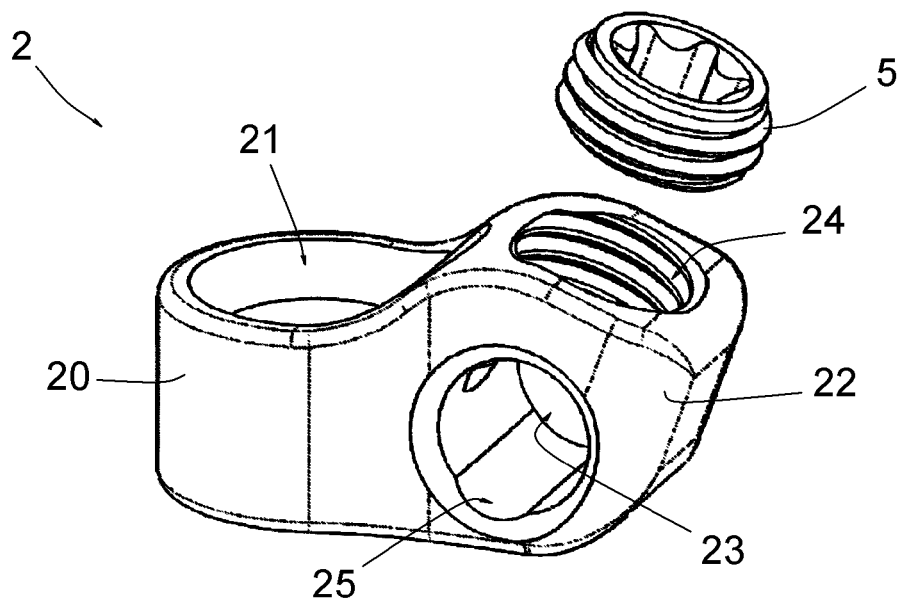
FIG. 1 is a perspective view of a clamping part in a first embodiment.
Figure 2:
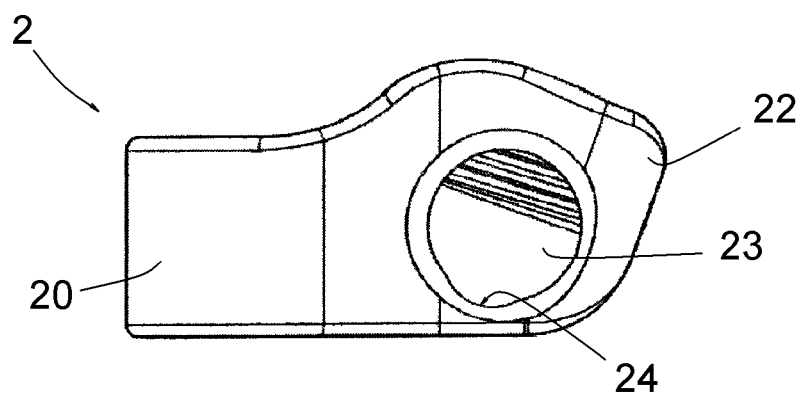
FIG. 2 is a side view of this clamping part.
Figure 3:
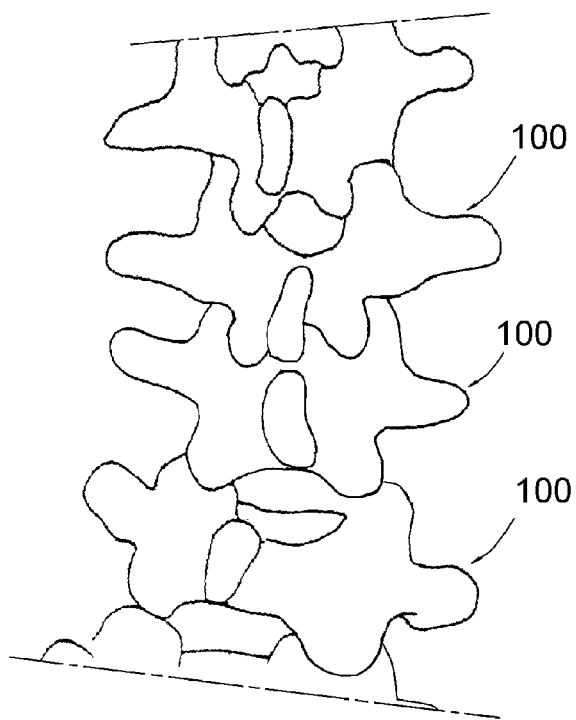
FIG. 3 is a posterior view of a part of a spine having a scoliosis and in which the vertebrae are rotated on the convex side of this spine, which is the right side of this figure.

With reference now to FIGS. 1 and 2, each of the clamping parts 2 in a preferred embodiment includes a first part 20 delineating a first hole 21 for engagement on the threaded portion 11 of one of the polyaxial screws 1 and a second part 22 delineating a second hole 23 for receiving one of the linking rods 3. The second part 22 also delineates a third hole 24, which communicates with the second hole 23 and is tapped so as to receive one of the set screws 5. The second hole 23 includes a groove 25 opposite the third hole 24. In further embodiments, the clamping parts 2, tightening nuts 4, and set screws 5 may be as described in Published U.S. application 2006/167455, the contents of which also are incorporated herein by reference.

Figure 5:
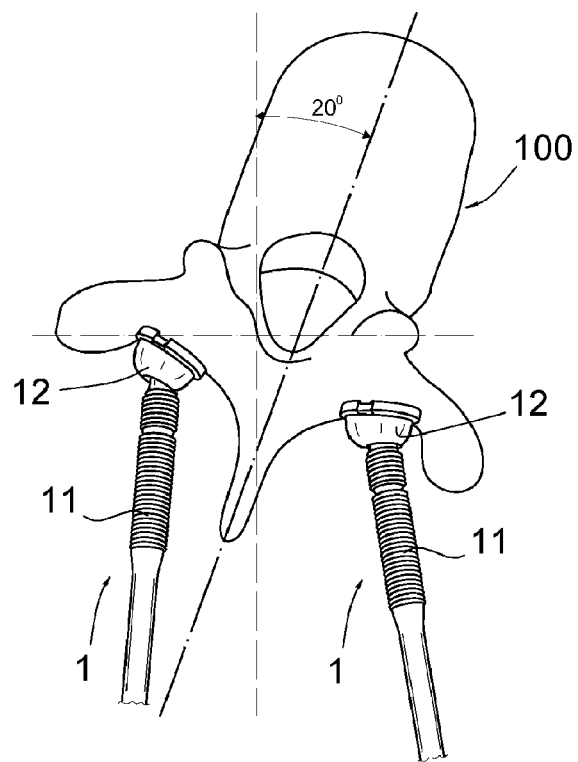
FIG. 5 is a transverse view of the spine, in a first step of the method.
Figure 6:
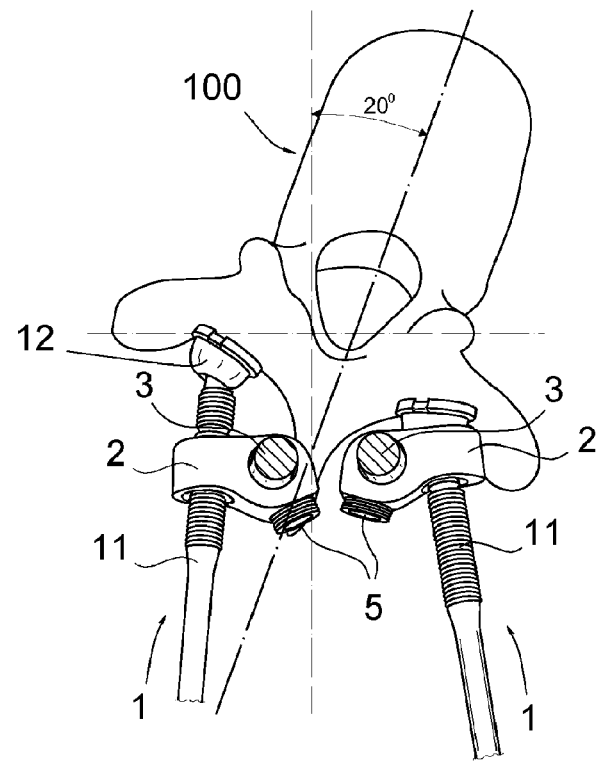
FIG. 6 is a view of the spine similar to FIG. 5, in a subsequent step of the method.

The method is now described with reference to the series of steps shown in FIGS. 5 to 12. Initially, two series of the polyaxial screws 1 are implanted in the respective left and right pedicules of the vertebrae 100, such as shown in FIG. 5 (the series of polyaxial screws 1 being visible in FIG. 4). As shown in FIG. 6, the clamping parts 2 are added to the polyaxial screws 1, one of the linking rods 3 is connected to one of the series, and another of the linking rods 3 is connected to a second of the series. The set screws 5 that engage the respective linking rods 3 are not tightened at this stage.

Figure 7:
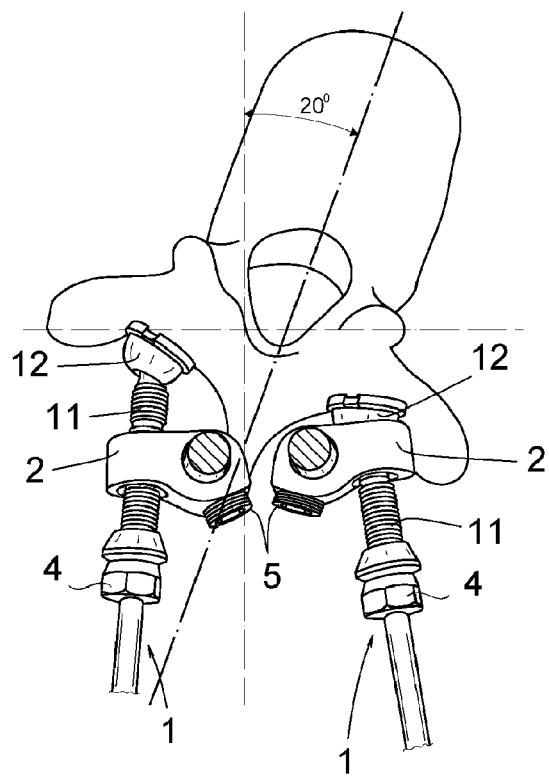
FIG. 7 is a view of the spine similar to FIG. 6, in a subsequent step of the method.
Figure 8:
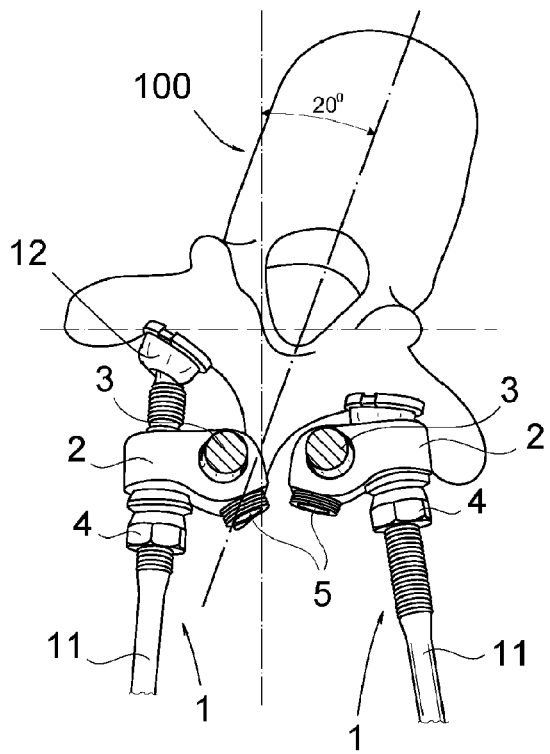
FIG. 8 is a view of the spine similar to FIG. 7, in a subsequent step of the method.

With reference to FIG. 7, tightening nuts 4 are engaged on respective threaded portions 11. The tightening nuts 4 for the series of polyaxial screws 1 on the convex side of the spine curvature (the convex side is the medial side on which the vertebral bodies are rotated, i.e. on the right in the figures) are tightened (FIG. 8) so as to tighten the clamping parts 2 of this series of polyaxial screws 1 against the bearing portions 12 of these screws 1 and to eliminate the polyaxiality of these screws 1.

Figure 9:
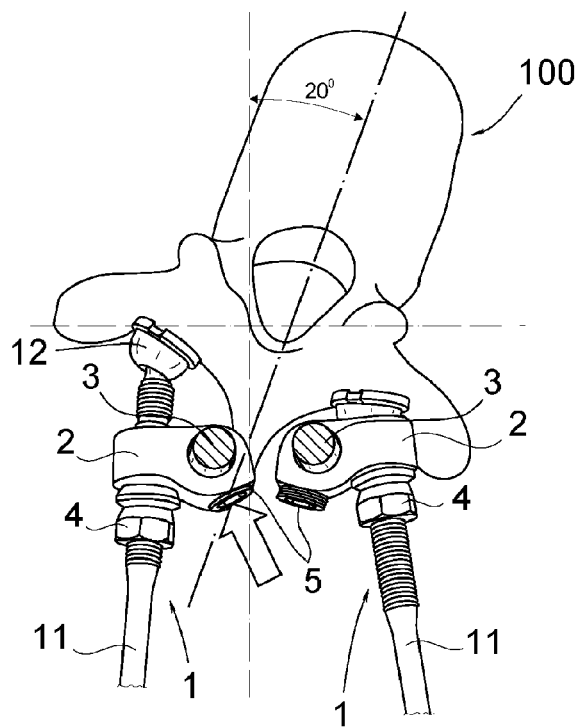
FIG. 9 is a view of the spine similar to FIG. 8, in a subsequent step of the method.

With reference now to FIG. 9, the set screws 5 of the series of polyaxial screws 1 on the concave side of the spine curvature (opposite the convex side) are tightened, so as to immobilize the linking rod 3 of this series relative to the clamping parts 2 of this series.

Figure 10:
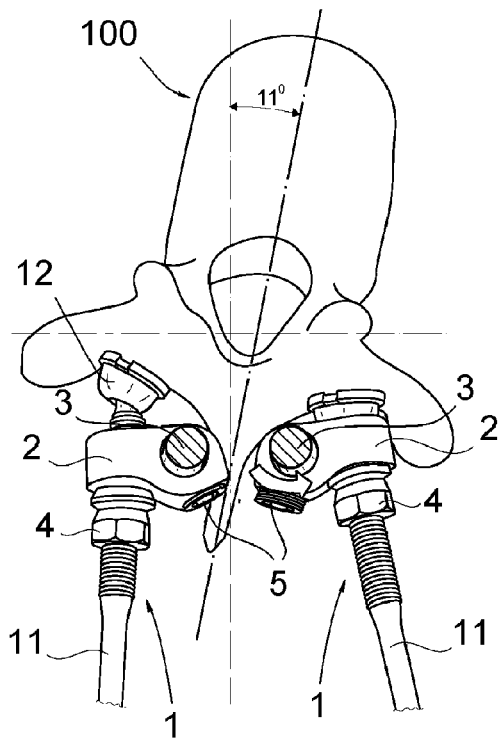
FIG. 10 is a view of the spine similar to FIG. 9, in a subsequent step of the method.
Figure 11:
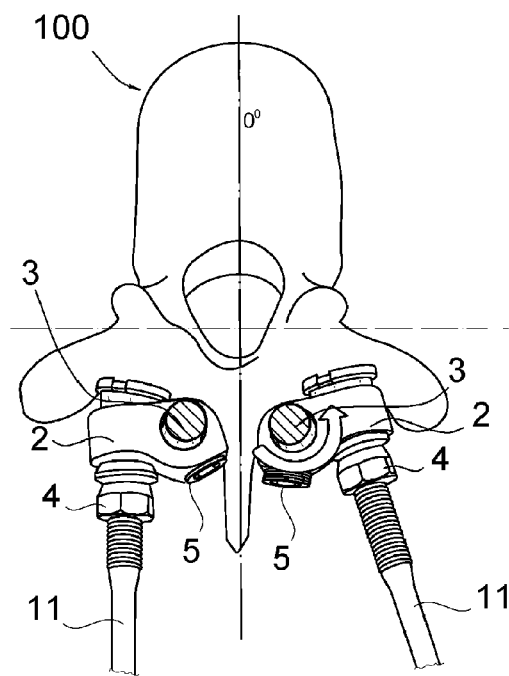
FIG. 11 is a view of the spine similar to FIG. 10, in a subsequent step of the method.

As shown in FIGS. 10-11, the tightening nuts 4 of the series of polyaxial screws 1 on the concave side of the spine curvature are tightened, so as to move the clamping parts 2 of this series in the direction of the bearing portions 12 of the polyaxial screws 1 of this series until these clamping parts 2 reach these bearing portions 12, thus achieving a rotation of the vertebrae 100 about the axis of the linking rod 3 located on the convex side of the spine curvature. As seem in FIG. 11, a total reduction of the rotation of the vertebra 100 may be achieved.

Figure 12:
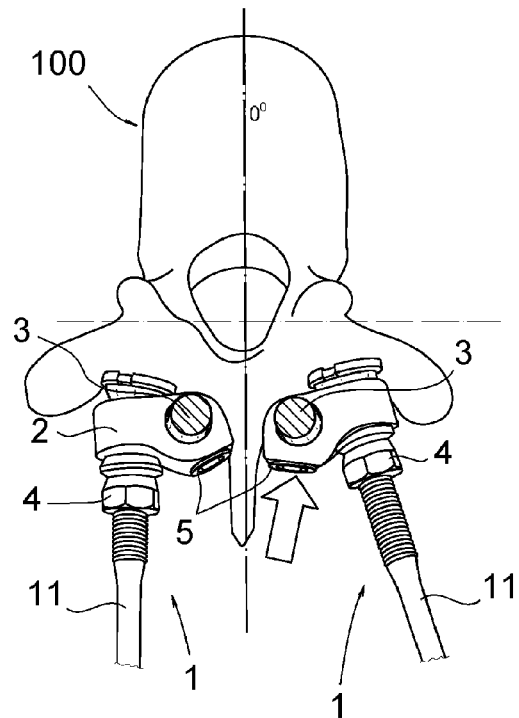
FIG. 12 is a view of the spine similar to FIG. 11, in a final step of the method, which corresponds to a sectional view taken along the line XII-XII of FIG. 4.

The set screws 5 of the series of screws 1 on the former convex side of the spine curvature are tightened, so as to immobilize the linking rod 3 of this series with respect to the clamping parts 2 of this series (FIG. 12.)

As is apparent, this method does not include additional leverage instruments connected to the vertebrae. Further, one or more vertebra are rotated in a progressive and controlled way. Suitable torque instruments may be used to evaluate the stress applied.

While embodiments of the present invention have been described in the foregoing specification and drawings, it is to be understood that the present invention is defined by the following claims when read in light of the specification and drawings.

What is claimed is:

1. A method for rotating a vertebra or vertebrae in a spine that is curved, comprising the steps of:
   using a vertebral osteosynthesis device that includes,
      polyaxial screws, each polyaxial screw having an anchoring distal part for anchoring to a vertebra, a bearing portion on the proximal part of said anchoring distal part, and a proximal threaded part articulated with respect to the anchoring distal part,
      two linking rods,
      clamping parts, each of which comprises a first hole for receiving one of said linking rods and a second hole for engaging on said proximal threaded part until bearing on said bearing portion,
      tightening nuts, each of which can be screwed on said proximal threaded parts of said polyaxial screws so as to tighten one of said clamp part on said bearing portion, and, doing so, to eliminate the polyaxiality of said one polyaxial screw, and
      tightening means on each of said clamping parts, each of which allows tightening one of said linking rods in said first hole so as to immobilize the linking rod with respect to the clamping part;
   implanting a first series of said polyaxial screws in vertebrae of the spine, on the convex side of the spine curvature, the convex side being the medial side on which the vertebral bodies are rotated, and a second series of said polyaxial screws in vertebrae of the spine, on the concave side of the spine curvature, followed by
   i) inserting a first linking rod in a first series of said clamping parts and the second linking rod in a second series of said clamping parts,
   ii) orientating said proximal threaded parts of said first series of said polyaxial screws for allowing the engagement of said first series of clamping parts on said proximal threaded parts of said first series of said polyaxial screws,
   iii) orientating said proximal threaded parts of said second series of said polyaxial screws for allowing the engagement of said second series of clamping parts on said proximal threaded parts of said second series of said polyaxial screws, and
   iv) engaging said first series of said clamping parts on the proximal thread parts of said first series of said polyaxial screws and engaging said second series of said clamping parts on the proximal threaded parts of said second series of said polyaxial screws;
   engaging and completely tightening said tightening nuts on said proximal threaded parts of said first series of polyaxial screws, so as to tighten said first clamping parts against said bearing portions of said first series of polyaxial screws and to eliminate polyaxiality of said first series of polyaxial screws;
   engaging and partly tightening said tightening nuts on said proximal threaded parts of said second series of polyaxial screws, so as to position said second linking rod in a final position in which the second linking rod is substantially level with said first linking rod of said first series of screws substantially in a same transverse plane of the vertebrae;
   completely tightening the tightening means of said second series of said clamping parts, so as to immobilize said second linking rod with respect to said clamping parts of said second series of clamping parts in said final position;
   further tightening said tightening nuts on said second series of said polyaxial screws, so as to move said clamping parts of said second series of clamping parts in a direction of said bearing portions of said polyaxial screws of said second series until the respective said clamping parts reach the respective said bearing portions, thus causing a rotation of the vertebrae about a longitudinal axis of said first linking rod, a total reduction of the rotation of the vertebra being achieved when said tightening nuts on said second series of said polyaxial screws are completely tightened; and
   completely tightening said tightening means of said first series of clamping parts, so as to immobilize said first linking rod with respect to said clamping parts of said first series of clamping parts.

2. The method of claim 1, wherein each of said clamping parts further comprises a third hole that communicates with said second hole and each of said tightening means is a set screw received in said third hole, and wherein the steps of tightening said set screws includes tightening said set screw in said third hole into engagement with the respective said linking rod.

3. The method of claim 1, wherein each clamping part includes a first part delineating a first hole for engagement on said threaded proximal part of one of said polyaxial screws and a second part delineating a second hole for receiving one of said linking rods, the second part further delineating a third hole which communicates with said second hole and is tapped so as to receive a set screw.

4. The method of claim 3, wherein said second hole forms a groove opposite said third hole.

* * * * *